United States Patent [19]

Ikeda et al.

[11] Patent Number: 4,608,580

[45] Date of Patent: Aug. 26, 1986

[54] HEAT-SENSITIVE RECORDING MATERIAL

[75] Inventors: Fukuji Ikeda, Takefu; Toshiaki Takahashi, Sabae, both of Japan

[73] Assignee: Nikka Chemical Industry Company Ltd., Fukui, Japan

[21] Appl. No.: 781,949

[22] Filed: Sep. 30, 1985

[30] Foreign Application Priority Data

Oct. 8, 1984 [JP] Japan .................................. 59-209768

[51] Int. Cl.4 ............................................. B41M 5/18
[52] U.S. Cl. ..................................... 346/216; 346/217; 346/225; 427/150
[58] Field of Search ............... 346/204, 216, 217, 218, 346/220, 221, 225; 427/150, 151, 152

[56] References Cited

U.S. PATENT DOCUMENTS 4,453,744  6/1984  Würmli et al. ...................... 346/216
4,536,779  8/1985  Nachbur et al. .................... 346/216

Primary Examiner—Bruce H. Hess
Attorney, Agent, or Firm—McAulay, Fields, Fisher, Goldstein & Nissen

[57] ABSTRACT

A heat-sensitive recording material comprising a support and, formed thereon, a heat-sensitive color-forming layer comprising a colorless or light-colored leuco dye as a color former and a phenolic compound as a color developer, wherein the color developer comprises 3,3'-diallyl-4,4'-dihydroxydiphenylsulfone as an effective ingredient.

3 Claims, No Drawings

HEAT-SENSITIVE RECORDING MATERIAL

BACKGROUND OF THE INVENTION (1) Field of the Invention

The present invention relates to a heat-sensitive recording material. More particularly, the present invention relates to a heat-recording material which is colored at a high density at a low temperature and in which deterioration of the colored zone by a plasticizer, oil, water, light or the like is prevented and the so-called storability is improved.

(2) Description of the Related Art

A heat-recording material comprising a heat-sensitive coloring layer capable of being colored by heating, which is formed on a support such as paper, artificial paper, plastic film or the like, is used for a thermal printer of a facsimile device, an electronic table computer or a microcomputer or a thermopen recorder of an electrocardiograph or an analysis device or for formation of a passenger ticket or a POS label at a super market.

This heat-sensitive recording material is ordinarily prepared by separately pulverizing a colorless or light-colored leuco dye of the lactone, lactam or spiropyran type as a color former and a color developer capable of reacting with the color former under heating to form a color, by using a ball mill or sand mill to form dispersions, adding a binder to the dispersions, mixing the dispersions, adding a wax, a surface active agent, a defoaming agnet, an inorganic pigment and the like to the mixture according to need, and coating and drying the composition on a support such as paper.

Various phenolic compounds have heretofore been used as the color developer, and bisphenol A (isoprpylidene diphenol) is especially frequently used. The melting point of this phenolic compound is 156° to 158° C. and the color-forming temperature can be reduced by a compound used in combination, but the color-forming temperature is still high and it is difficult to cope with a recent requirement for enhancement of the printing speed. Furthermore, in a heat-sensitive recording material comprising bisphenol A as a color developer, deterioration of the color-formed zone is caused by contact with a vinyl chloride sheet or by oil, water, light or the like, resulting in discoloration of the color-formed zone, or coloration is caused in the non-colored zone.

Recently, a color developer comprising benzyl p-hydroxybenzoate has been developed as a color developer suitable for high-speed printing and when this color developer is used, printing can be performed at a lower temperature. However, the above-mentioned deterioration becomes conspicuous in a heat-sensitive recording material comprising benzyl p-hydroxybenzoate as a color developer.

A heat-sensitive recording material comprising bisphenol S as the color developer is excellent in the storability characteristics of the colored zone, such as plasticizer resistance, oil resistance, water resistance and light resistance, and this heat-sensitive material is used in a special field where the heat-sensitive material is coated on a transparent vinyl chloride sheet or where the heat-sensitive material is used for the production of sheets which are readily contacted with hands, such as tickets and passes. However, bisphenol S is disadvantageous in that the color-forming temperature is high.

Under this background, development of a color developer having a good storability and a low color-forming temperature is eagerly desired.

SUMMARY OF THE INVENTION

We made research with a view to realizing the above desire, and as the result, we have now completed the present invention.

It is therefore a primary object of the present invention to provide a heat-sensitive recording material in which the color-forming temperature is reduced and the deterioration by a plasticizer contained in a vinyl chloride sheet or the deterioration by oil, water or light is prevented.

In accordance with the present invention, there is provided a heat-sensitive recording material comprising a support and, formed thereon, a heat-sensitive color-forming layer comprising a colorless or light-colored leuco dye as a color former and a phenolic compound as a color developer, wherein the color developer comprises 3,3'-diallyl-4,4'-dihydroxydiphenylsulfone as an effective ingredient.

DESCRIPTION OF THE PREFERRED EMOBIDMENTS

As the colorless or light-colored color former valuably used for the heat-sensitive recording material of the present invention, there can be mentioned Crystal Violet Lactone, Malachite Green Lactone, 3,3-bis(p-dimethylaminophenyl)-6-aminophthalide, 3,3-bis(p-dimethylaminophenyl)-6-(p-toluenesulfonamido)phthalide, 3-diethylamino-7-chlorofluoran, 3-diethylamino-7-phenylfluoran, 3-cyclohexylamino-6-chlorofluoran, 3-N-methyl-N-cyclohexylamino-6-methyl-7-anilinofluoran and 1,3,3-trimethyl-6'-chloro-8'-methoxyindolinobezospiropyran. These color formers may be used singly or in the form of a mixture of two or more of them. The mixing ratio may be appropriately changed according to the kind of the color developer.

The color developer valuably used in the present invention comprises 3,3'-diallyl-4,4'-dihydroxydiphenylsulfone (hydroxyl groups are present as the substituents at the 4,4'-positions). Diallyldihydroxydiphenylsulfones having the 2,4-positions or 2,2'-positions substituted with hydroxyl groups may be contained within an allowable range. Furthermore, mono-, tri- or tetraallyl compounds may be contained within an allowable range. By the term "allowable range", it is meant that coloration of the heat-sensitive recording material per se is not conspicuous. Incidentally, if the contents of such impurity compounds are high, the heat-sensitive recording material per se is colored.

Diallylbisphenol S (diallyldihydroxydiphenylsulfone) valuable in the present invention may be used singly or in combination with other color developer, for example, bisphenol S (dihydroxydiphenylsulfone) or bisphenol A or moreover with a sensitizer.

As the technique for coating the color former and the color developer on a support such as paper, there can be mentioned a customary method in which the color former and the color developer, together with other additives, are dispersed in a binder and the dispersion is coated on a support. As the binder, there can be mentioned hydroxyethyl cellulose, carboxymethyl cellulose, polyvinyl alcohol, starch, polyacrylic acid, polyacrylamide and a styrene/maleic acid copolymer.

Since color formation is caused at a low temperature when the heat-sensitive recording material of the present inventin is used, high-speed printing becomes possible, and deterioration by the contact with a vinyl chloride sheet or deterioration by oil, water or light is hardly caused and printed letters can be obtained with good storability and good handling stability.

The present invention will now be described in detail with reference to the following examples. Incidentally, all of "parts" and "%" in the examples are by weight.

SYNTHESIS EXAMPLES

(A) Synthesis of Diallyl Ether of Bisphenol S

To a solution comprising 250 parts of bisphenol S, 600 parts of methanol, 400 parts of water and 85 parts of caustic soda was dropped 250 parts of allyl bromide at $60° \pm 5°$ C., and reaction was carried out for 3 hours at this temperature. The reaction mixture was cooled and the crystal was recovered by filtratron at 25° C. The crystal was washed with a mixture comprising 600 parts of methanol and 400 parts of water, followed by drying. The intended compound was obtained in an amount of 270 parts and the yield was 82%. The melting point of the obtained compound was 141° to 145° C.

(B) Synthesis of Diallylbisphenol S

In an atmosphere of $N_2$ gas, 250 parts of the diallyl ether of bisphenol S synthesized in (A) above was heated and thermal dislocation was conducted at 195° to 210° C. for 6 hours. The termination of the reactron was determined when the reaction product was completely dissolved in a dilute aqueous solution of caustic soda in an amount smaller than the amount equimolar to caustic soda. The reaction product was taken out, solidified and pulverized. The amount obtained of the reaction product was 238 parts, and the yield was 95%. The melting point of the reaction product was 145° to 150° C. The acid value of phenolic OH was 333 (the theoretical value being 340).

EXAMPLE 1

The following liquids A and B were separately prepared as the heat-sensitive color-forming layer-forming liquid, and they were finely pulverized and dispersed by using a sand mill so that the particle size was smaller than $5\mu$.

| Liquid A (Color Former Dispersion) | |
|---|---|
| 3-N—methyl-N—cyclohexylamino-6-methyl-7-anilinofluoran | 1.5 parts |
| 10% Aqueous solution of polyvinyl alcohol | 2.0 parts |
| Water | 0.5 part |
| Liquid B (Color Developer Dispersion) | |
| Diallylbisphenol S (prepared in the Synthesis Examples) | 3.0 parts |
| 10% Aqueous solution of polyvinyl alcohol | 13 parts |
| Water | 5.5 parts |

To the above liquid B were added 5.0 parts of kaolin, 19 parts of a 10% aqueous solution of polyvinyl alcohol and 8 parts of water, and the mixture was added to the liquid A. Then, the mixture was coated to wood free paper having a basis weight of 65 g/m² so that the amount coated was about 4.2 g/m² after drying. The coated paper was air-dried to obtain a heat-sensitive recording paper.

EXAMPLE 2

The procedures of Example 1 were repeated in the same manner except that the amount of diallylbisphenol S in the liquid B was changed to 1.2 parts and the remaining 1.8 parts of diallylbisphenol S was replaced by bisphenol S.

EXAMPLE 3

The procedures of Example 1 were repeated in the same manner except that the amount of diallylbisphenol S in the liquid B was changed to 1.2 parts and the remaining 1.8 parts of diallylbisphenol S was replaced by bisphenol A.

EXAMPLE 4

The procedures of Example 1 were repeated in the same manner except that 3.0 parts of diallylbisphenol S was used in combination of 1.0 part of a diallyl ether of bisphenol S as a sensitizer in the liquid B.

COMPARATIVE EXAMPLE 1

The procedures of Example 1 were repeated in the same manner except that all the amount of diallylbisphenol S in the liquid B was replaced by bisphenol S.

COMPARATIVE EXAMPLE 2

The procedures of Example 1 were repeated in the same manner except that all the amount of diallylbisphenol S in the liquid B was replaced by bisphenol A.

COMPARATIVE EXAMPLE 3

The procedures of Example 1 were repeated in the same manner except that all the amount of diallylbisphenol S in the liquid B was replaced by benzyl p-hydroxybenzoate.

CAPACITY TESTS

The capacities of the heat-sensitive recording papers obtained in the foregoing examples and comparative examples were tested according to the following methods.

(1) Color-Developing Property

In a scorch tester, the sample was heated for the color formation at a predetermined temperature for 5 seconds. The heating temperature was elevated by intervals of 10° C. The reflectance was measured by a Hunter color difference meter (550 nm).

(A) The background fogging was calculated according to the followrng formula:

$$\frac{I_0 - I_1}{I_0} \times 100$$

Incidentally, a smaller value of the background fogging is better.

(B) The rise and fall temperatures and the coloring efficiencies were determined in the following manner.

The measurement temperature and the coloring efficiency $$\left( \frac{I_1 - I_2}{I_1} \times 100 \right)$$

at this temperature were plotted on a graph and tangent lines were drawn. The rise temperature and the corresponding coloring efficiency and the fall temperature and the corresponding coloring efficiency were determined from the intersection points. A heat-sensitive recording paper in which the difference between the rise temperature and the fall temperature is small is suitable for high-speed printing.

Incidentally, $I_0$ represents the reflectance of the starting paper before the coating, $I_1$ represents the reflectance of the heat-sensitive recording paper before the color formation, and $I_2$ represents the reflectance after the color formation.

(2) Color Developing Property after Dipping in Water

The heat-sensitive recording paper was dipped in water at 20° C. for 2 hours and then air-dried. Color formation was effected at 160° C. for 5 seconds [at 180° C. in case of bisphenol S (Comparative Example 1) and at 140° C. in case of benzyl p-hydroxybenzoate (Comparative Example 3)], and the reflectance $I_3$ was measured. Color formation was similarly effected without dipping into water, and the reflectance $I_2$ was measured. The water resistance, that is, the resistance against dropping in water, was evaluated based on the color-developing property residual ratio, $$\frac{I_1 - I_3}{I_1 - I_2} \times 100.$$

A higher residual ratio is better.

(3) Resistance against Discoloration by Plasticizer

Color formatin was carried out under the same temperature and time conditions as described in (2) above, and the recording paper was closely stuck to a vinyl chloride sheet containing about 30% of dioctyl phthalate and allowed to stand still in this state at 60° C. for 8 hours, and the reflectance $I_4$ was measured. The resistance against discoloration by the plasticizer was evaluated based on the residual ratio, $$\frac{I_1 - I_4}{I_1 - I_2} \times 100.$$

A higher residual ratio is preferred.

(4) Resistance against Discoloration by Castor Oil

Color formation was carried out under the same temperature and time conditions as described in (2) above, and castor oil was thinly coated on the recording paper and the recording paper was allowed to stand still in this state at 40° C. for 3 days. The reflectance $I_5$ was measured. The resistance against discoloration by castor oil was evaluated based on the residual ratio, $$\frac{I_1 - I_5}{I_1 - I_2} \times 100.$$

A higher residual ratio is preferred.

(5) Resistance against Discoloration by Water

Color formation was carried out under the same temperature and time conditions as described in (2) above, and the recording paper was immersed in water at 20° C. for 2 hours and air-dried. The reflectance $I_6$ was measured, and the resistance against discoloration by water was evaluated based on the residual ratio, $$\frac{I_1 - I_6}{I_1 - I_2} \times 100.$$

A higher residual ratio is preferred.

(6) Resistance against Discoloration by Light

Color formation was carried out under the same temperature and time conditions are described in (2) above, and the recording paper was allowed to stand still in an ultraviolet ray long life fade-ometer at 63° C. for 20 hours. The reflectance $I_7$ was measured. The resistance against discoloration by light was evaluated based on the residual ratio, $$\frac{I_1 - I_7}{I_1 - I_2} \times 100.$$

A higher residual ratio is preferred.

The obtained results are shown in Table 1.

TABLE 1

| | Liquid B | | | Color Developing Properties | | |
| | | | | Rise Temperature and | Fall Temperature and | Difference between |
| | Color Developer | Sensitizer | Background Fogging | Coloring Efficiency | Coloring Efficiency | Rise and Fall temperatures |
|---|---|---|---|---|---|---|
| Example 1 | compound of present invention* | not added | 2.4 | 92° C. 5.0% | 112° C. 88.0% | 20° C. |
| Example 2 | compound of present invention* plus bisphenol S | not added | 2.5 | 82° C. 6.0% | 102° C. 86.0% | 20° C. |
| Example 3 | compound of present invention* plus bisphenol A | not added | 2.5 | 90° C. 5.0% | 115° C. 87.0% | 25° C. |
| Example 4 | compound of present invention* | diallyl ether of bisphenol S | 2.2 | 87° C. 7.0% | 100° C. 87.0% | 13° C. |
| Comparative Example 1 | bisphenol S | not added | 2.4 | 155° C. 7.0% | 178° C. 87.0% | 23° C. |

TABLE 1-continued

| | | | | | | |
|---|---|---|---|---|---|---|
| Comparative Example 2 | bisphenol S | not added | 2.4 | 98° C. 6.0% | 135° C. 90.0% | 37° C. |
| Comparative Example 3 | benzyl p-hydroxybenzoate | not added | 2.2 | 74° C. 8.0% | 90° C. 90.0% | 16° C. |

| | Color Developing Properties | Resistance against Discoloration (residual ratio) | | | |
|---|---|---|---|---|---|
| | Color Developing Property after Dipping in Water (residual ratio) | Resistance against Discoloration by plasticizer | Resistance against Discoloration by Castor Oil | Resistance against Discoloration by Water | Resistance against Discoloration by Light |
| Example 1 | 99% | 94% | 83% | 99.5% | 92.5% |
| Example 2 | 99% | 95% | — | 99.5% | 93% |
| Example 3 | — | 76% | — | — | — |
| Example 4 | 99% | 93% | — | 90% | 90% |
| Comparative Example 1 | 30% | 98% | 91% | 94% | 94% |
| Comparative Example 2 | 20% | 49% | 66% | 97% | 69% |
| Comparative Example 3 | 97% | 30% | 51% | 58% | 54% |

Note
*diallylbisphenol S prepared in Synghesis Example (B)

From the results shown in Table 1, it is seen that in the heat-sensitive recording material comprising the color developer of the present invention (diallybisphenol S), color formation is caused at a much lower temperature than in case of the heat-sensitive recording material comprising bisphenol S and at a slightly lower temperature than in case of the heat-sensitive recording material comprising bisphenol A. Moreover, it is seen that the heat-sensitive recording material comprising the color developer of the present invention is especially characteristic and advantageous in that the water resistance is very good and even after dipping in water, heat printing can be performed without any deterioration. Furthermore, it is seen that the color developer of the present invention is excellent over bisphenol A, bisphenol B and benzyl p-hydroxybenzoate in the storability characteristics such as plasticizer resistance, oil resistance, water resistance and light resistance and the defects of the conventional color developers are substantially overcome in the color developer of the present invention.

We claim:

1. A heat-sensitive recording material comprising a support and, formed thereon, a heat-sensitive color-forming layer comprising a colorless or light-colored leuco dye as a color former and a phenolic compound as a color developer, wherein the color developer comprises 3,3'-diallyl-4,4'-dihydroxydiphenylsulfone as an effective ingredient.

2. A heat-sensitive recording material according to claim 1, wherein the colorless or light-colored leuco dye is selected from Crystal Violet Lactone, Malachite Green Lactone, 3,3-bis(p-dimethylaminophenyl)-6-aminophthalide, 3,3-bis(p-dimethylaminophenyl)-6-(p-toluenesulfonamido)phthalide, 3-diethylamino-7-chlorofluoran, 3-diethylamino-7-phenylfluoran, 3-cyclohexylamino-6-chlorofluoran, 3-N-methyl-N-cyclohexylamino-6-methyl-7-anilinofluoran and 1,3,3-trimethyl-6'-chloro-8'-methyoxyindolinobezospiropyran, and mixtures of two or more thereof.

3. A heat-sensitive recording material according to claim 1, wherein the color developer further comprises bisphenol S or bisphenol A in combination with 3,3'-diallyl-4,4'-dihydroxydiphenylsulfone.

* * * * *